United States Patent
Jascomb et al.

(10) Patent No.: US 11,589,633 B2
(45) Date of Patent: Feb. 28, 2023

(54) MULTI-LAYER VISOR SYSTEM FOR SURGICAL HOOD

(71) Applicant: O&M Halyard, Inc., Mechanicsville, VA (US)

(72) Inventors: Jerald T. Jascomb, Roswell, GA (US); Namita A. Mithani, Alpharetta, GA (US)

(73) Assignee: O&M Halyard, Inc., Mechanicsville, VA (US)

( * ) Notice: Subject to any disclaimer, the term of this patent is extended or adjusted under 35 U.S.C. 154(b) by 101 days.

(21) Appl. No.: 16/681,911

(22) Filed: Nov. 13, 2019

(65) Prior Publication Data
US 2021/0137205 A1   May 13, 2021

(51) Int. Cl.
*A42B 3/26* (2006.01)
*A61F 9/04* (2006.01)
(Continued)

(52) U.S. Cl.
CPC ........... *A42B 3/26* (2013.01); *A61F 9/045* (2013.01); *B32B 3/08* (2013.01); *B32B 5/022* (2013.01);
(Continued)

(58) Field of Classification Search
CPC ... A42B 3/26; A61F 9/045; A61F 9/02; B32B 7/06; B32B 27/08; A41D 13/1218; A41D 13/1184; A41D 13/1153
See application file for complete search history.

(56) References Cited

U.S. PATENT DOCUMENTS 3,872,516 A * 3/1975 Bird ................. A42B 1/045
2/202
5,253,642 A * 10/1993 Stackhouse ........... A41D 13/11
128/201.25
(Continued)

FOREIGN PATENT DOCUMENTS

AU       2012254955 B2   12/2014
WO    WO 2014/197344 A1   12/2014

OTHER PUBLICATIONS

International Search Report and Written Opinion for PCT/US2020/059639, dated Mar. 3, 2021, 16 pages.

*Primary Examiner* — Joanna Pleszczynska
(74) *Attorney, Agent, or Firm* — Dority & Manning, P.A.

(57) ABSTRACT

A multi-layer visor system for a surgical hood or garment is provided. The system includes a base film layer and one or more removable film layers that are coextruded at high temperature to form a sterile surface between each of the film layers should the surgeon elect to peel away a soiled or splattered removable film layer during the course of a surgical procedure so that an unobstructed view can be maintained. Thus, no separate sterilization step is required in order to sterilize the layers of the visor system. Each of the removable film layers can additionally include a tab having distinctive features in order to enable a wearer to easily distinguish between the tabs in order to make it easier for a wearer to know which tab to pull first to remove the outermost removable film layer. Further, because the tabs are located about the perimeter of the removable films, viewing is not obscured, yet the film layers are held securely in place until easily removed from the underlying removable film layer or base film layer.

17 Claims, 8 Drawing Sheets

(51) Int. Cl.
  *B32B 7/06*      (2019.01)
  *B32B 27/08*     (2006.01)
  *A41D 13/11*     (2006.01)
  *A41D 13/12*     (2006.01)
  *B32B 3/08*      (2006.01)
  *B32B 5/02*      (2006.01)
  *B32B 27/12*     (2006.01)

(52) U.S. Cl.
  CPC ............... *B32B 7/06* (2013.01); *B32B 27/08* (2013.01); *B32B 27/12* (2013.01); *B32B 2250/244* (2013.01); *B32B 2307/402* (2013.01); *B32B 2437/00* (2013.01); *B32B 2571/00* (2013.01)

(56) References Cited

U.S. PATENT DOCUMENTS

| | | | |
|---|---|---|---|
| 5,344,691 | A | 9/1994 | Hanschen et al. |
| 6,388,813 | B1 | 5/2002 | Wilson et al. |
| 8,129,450 | B2 | 3/2012 | Wood et al. |
| 8,261,375 | B1 * | 9/2012 | Reaux ............... A41D 13/1184 2/424 |
| 8,407,818 | B2 | 4/2013 | VanDerWoude et al. |
| 9,415,561 | B2 | 8/2016 | Lindquist et al. |
| 10,427,385 | B2 | 10/2019 | Wilson et al. |
| 2007/0264520 | A1 | 11/2007 | Wood et al. |
| 2015/0183178 | A1 | 7/2015 | Lindquist et al. |
| 2016/0023442 | A1 * | 1/2016 | Faris ............... B32B 27/40 428/447 |
| 2017/0071792 | A1 * | 3/2017 | Wilson ............... A61F 9/029 |

\* cited by examiner

MULTI-LAYER VISOR SYSTEM FOR SURGICAL HOOD

FIELD OF THE INVENTION

The subject matter of the present invention relates generally to the visor component of surgical hoods that can be used in conjunction with surgical gowns, helmets, and ventilation systems worn by medical providers in the operating room or people in any other environment where exposure to hazardous materials and liquids is a risk.

BACKGROUND

Surgeons and other healthcare providers often wear a combination of a nonwoven-based surgical suit or gown, a hood with a visor, and an air cooling or ventilation system during operating procedures, particularly orthopedic total joint replacement surgeries such as arthroplasties and revisions of the knee, hip, and shoulder, in order to ensure sterile conditions in the operating room, protect the wearer, and create a comfortable environment for the wearer. During the course of such surgeries, aerosolized or droplets of biological fluid can spray onto the visor, obstructing the view of the surgeon or other healthcare provider. Thus, in order to provide surgeons and other healthcare providers with improved visibility, the visor can include one or more removable transparent films, where the surgeon or other healthcare provider can remove or peel away the transparent film should it become covered with biological fluids, tissue, etc., thus exposing a clean, unobstructed surface of an additional removable transparent film or the transparent base film of the visor positioned below the transparent film that was removed. The transparent films must be sterile, and because the transparent films are in close contact with each other, adequate sterilization of the transparent films is often problematic.

Currently, ethylene oxide (EO) gas is used to sterilize all nonwoven-based surgical suits or gowns and hoods. However, a problem exists when using EO gas to sterilize visors with multiple transparent films, as the transparent films are typically in direct contact with each other and such polyester films are not gas-permeable. The direct contact between film layers and non-permeability of the polyester film thereby prevents the EO gas from penetrating through the outermost, exposed transparent film to sterilize the underlying additional transparent films present.

In some cases, radiation sterilization, such as gamma or e-beam irradiation, is used to pre-sterilize visors with multiple transparent films in order to sterilize the underlying transparent films that are not exposed. However, radiation sterilization of the visor must occur prior to affixing the visor to a hood or suit of a personal protection system. If radiation sterilization were used on the final personal protection system, e.g., hood including the visor and one or more nonwoven-based gowns or suits, the polypropylene nonwoven fabric would suffer degradation that may include loss of strength, durability, or integrity, as well as generating unwanted odors, as a result of the radiation. In addition, stability of the nonwoven fabric over time may suffer unacceptably as a result of such radiation. Thus, the pre-sterilization step of radiation is required to sterilize the multi-layer visor prior to affixing the visor to the personal protection system, which is followed by sterilization of the final converted personal protection system using EO gas. However, the performance of separate pre-sterilization of the multi-layer visor in addition to EO gas sterilization of the final surgical hood or personal protection system significantly increases both the time and the cost of manufacturing.

Consequently, a need exists for a visor having a transparent base film and one or more transparent removable films attached thereto that does not require a separate step of pre-sterilization of the visor prior to incorporating the visor into a hood and/or surgical suit or gown with which it will be worn. In particular, a visor having two or more transparent removable films with one or more features to distinguish between each transparent removable film to improve ease of removal would also be useful.

SUMMARY

The present invention is directed to a method of manufacturing a multi-layer visor system for a personal protection system. The multi-layer visor system includes a base film layer and a first removable film layer releasably coupled to an outer-facing surface of the base film layer, wherein the base film layer defines a perimeter and the first removable film layer defines a perimeter, wherein the perimeter of the first removable film layer is contained completely within the perimeter of the base film layer. The method includes the steps of: coextruding a visor film including a base film and a first removable film; cutting the base film and the first removable film in the shape of the perimeter of the base film layer; and cutting the first removable film in the shape of the perimeter of the first removable film layer.

In one particular embodiment, the outer-facing surface of the base film layer is sterile without a separate sterilization step.

In another embodiment, the step of coextrusion is conducted at a temperature of at least about 535 degrees Fahrenheit (280 degrees Celsius).

In an additional embodiment, the multi-layer visor system further includes a second removable film layer releasably coupled to an outer-facing surface of the first removable film layer, wherein the second removable film layer defines a perimeter, wherein the perimeter of the second removable film layer is contained completely within the perimeter of the base film layer; wherein the step of coextruding the visor composite film includes coextruding a second removable film with the first removable film and the base film; further including a step of cutting the second removable film to form the perimeter of the second removable film layer. Moreover, the perimeter of the second removable film layer can be contained completely within the perimeter of the first removable film layer. Further, the outer-facing surface of the first removable film layer is sterile without a separate sterilization step.

In yet another embodiment, the step of cutting the base film and the first removable film to form a visor shape having a perimeter is performed by die-cutting.

In still another embodiment, the method further includes steps of: aligning a first strip of colored film with an upper edge of the perimeter of the first removable film layer adjacent to the first removable film layer; and cutting the first strip of colored film to form a first colored tab along the upper edge of the perimeter of the first removable film layer, wherein the first colored tab is configured to facilitate removal of the first removable film from the base film by a user. Moreover, the method can further include steps of: aligning a second strip of colored film with an upper edge of the perimeter of the second removable film layer adjacent to the second removable film layer; and cutting the second strip of colored film to form a second colored tab along the upper edge of the perimeter of the second removable film layer, wherein the second colored tab is configured to facilitate removal of the second removable film layer from the first removable film layer by a user.

The present invention is further directed to a multi-layer visor system for a personal protection system. The visor system includes a base film layer and a first removable film layer releasably coupled to an outer-facing surface of the base film layer. The base film layer and the first removable film layer are coextruded.

In one particular embodiment, the base film defines a perimeter and the first removable film layer defines a perimeter, wherein the perimeter of the first removable film is contained completely within the perimeter of the base film.

In another embodiment, an outer-facing surface of the base film layer is sterile.

In a further embodiment, the base film layer includes a polyester or a polycarbonate.

In yet another embodiment, the first removable film layer includes a polyester or a polycarbonate.

In an additional embodiment, the visor system includes an anti-reflective coating applied to an inner-facing surface of the base film layer.

In still another embodiment, the visor system includes a protective film releasably coupled to an inner-facing surface of the base film layer.

In one more embodiment, the first removable film layer includes a tab, wherein the tab facilitates removal of the first removable film layer from the base film layer.

In another embodiment, the first removable film layer includes a transparent viewing portion and a colored tab portion.

In a further embodiment, the visor system includes a second removable film layer releasably coupled to an outer-facing surface of the first removable film layer; wherein the first removable film layer and the second removable film layer are coextruded. Moreover, the base film layer defines a perimeter and the second removable film layer defines a perimeter, wherein the perimeter of the second removable film layer may be contained completely within the perimeter of the base film layer. Further, an outer-facing surface of the first removable film layer may be sterile. Moreover, the second removable film layer may include a polyester or a polycarbonate. Further, the second removable film layer can include a tab, wherein the tab facilitates removal of the second removable film layer from the first removable film layer. In addition, the first removable film layer can include a tab; further wherein the tab of the first removable film layer can be visually distinct from the tab of the second removable film layer.

The present invention is further directed to a multi-layer visor system as described above, wherein the surgical hood and the multi-layer visor system are sterile.

The present invention is also directed to a surgical gown including an integrated surgical hood and the multi-layer visor system as described above, wherein the surgical gown, the integrated surgical hood, and the multi-layer visor system are sterile.

The present invention is further directed to a personal protection system including a surgical gown and a separate surgical hood including the multi-layer visor system as described above, wherein the personal protection system is ethylene gas sterilized in a single package.

The present invention is further directed to a method of manufacturing a sterile protective surgical garment. The method includes the steps of: providing a multi-layer visor system as described above, wherein an outer-facing surface of the base film layer is sterile; providing a surgical hood comprising a nonwoven fabric material, a helmet, or other headwear; attaching the multi-layer visor system to an attachment area of the surgical hood, helmet, or headwear to form a protective surgical garment; and exposing the protective surgical hood to ethylene oxide gas to sterilize the protective surgical garment.

These and other features, aspects, and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION

Figure 1:
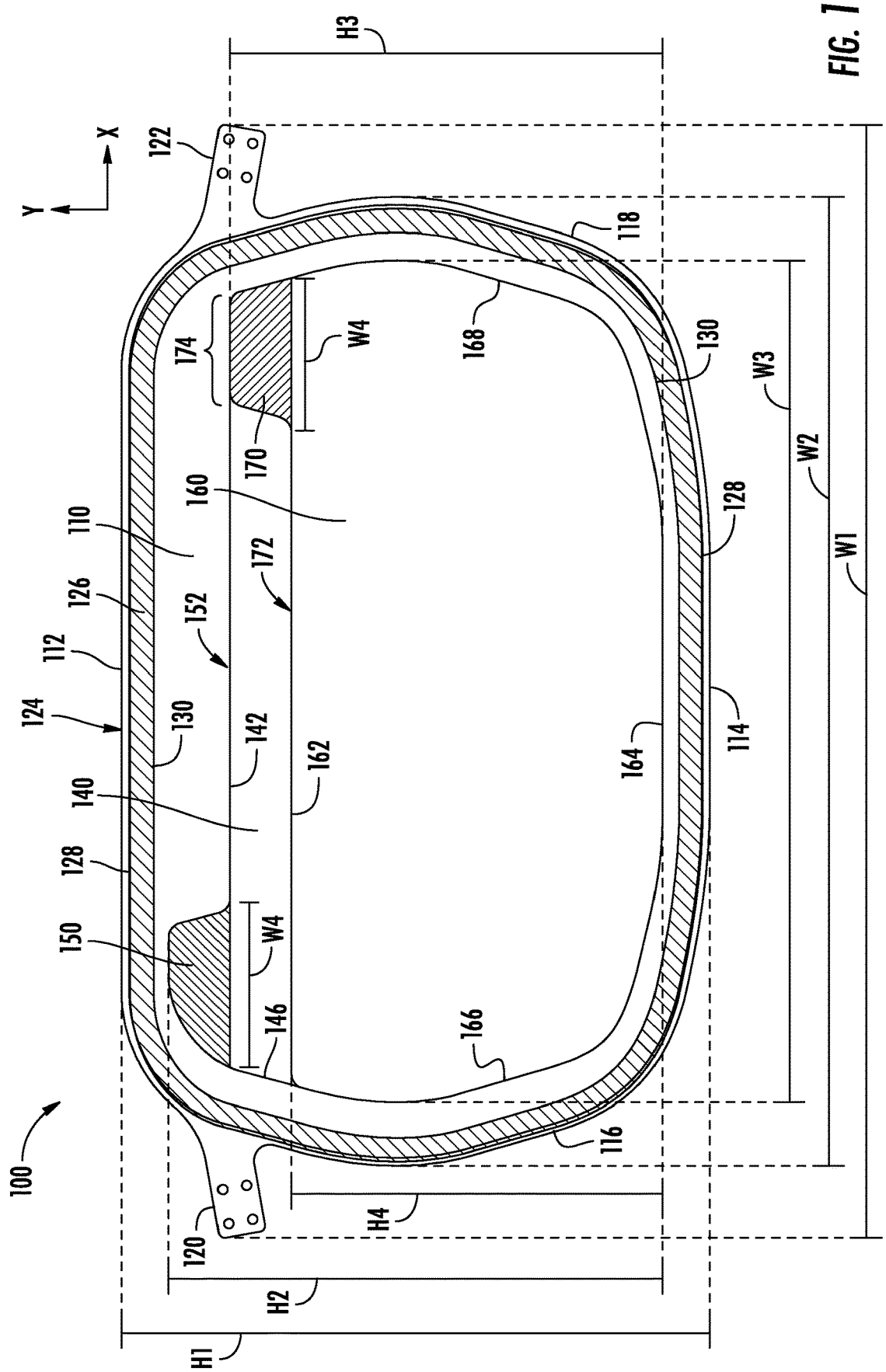
FIG. 1 illustrates a front view of a visor system according to one particular embodiment of the present invention.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

As used herein, the terms "about," "approximately," or "generally," when used to modify a value, indicates that the value can be raised or lowered by 5% and remain within the disclosed embodiment. Further, when a plurality of ranges are provided, any combination of a minimum value and a maximum value described in the plurality of ranges are contemplated by the present invention. For example, if ranges of "from about 20% to about 80%" and "from about 30% to about 70%" are described, a range of "from about 20% to about 70%" or a range of "from about 30% to about 80%" are also contemplated by the present invention.

Generally speaking, the present invention is directed to a visor system for a surgical hood that can be a component of a personal protection system, which can include a ventilation system in some embodiments. The present invention is further directed to a method of manufacturing the visor system, and a method of manufacturing a protective surgical garment incorporating the visor system and which does not require a step of pre-sterilization of the visor system. The visor system includes a base film layer and at least a first removable film layer releasably coupled to an outer-facing surface of the base film layer. The base film layer and the first removable film layer are coextruded. Specifically, in one embodiment, a first removable film is releasably coupled to an outer-facing surface of the base film and a second removable film is releasably coupled to an outer-facing surface of the first removable film, and each of the base film layer, first removable film layer, and second removable film layer are coextruded films. The films are coextruded together at sufficiently high temperatures to ensure sterility of each of the film layers. Sterility is conceptualized as the probability that a pathogenic organism will be present on a product. The safe sterility assurance level ("SAL") required by the Food and Drug Administration for medical devices, or "terminal kill," is $10^{-6}$, meaning a probability of one out of one million devices may contain a single organism. Put another way, terminal kill is generally associated with a 6-log reduction in bacteria. Because the temperatures of coextrusion of the films are sufficiently high to achieve "terminal kill", no separate sterilization step is required in order to sterilize each of the layers of the multi-layer visor system. Although it is to be understood that the transparent films of the visor system of the present invention can be formed from polycarbonate or polyester, which are materials through which ethylene oxide gas cannot penetrate, the high temperatures of the coextrusion of the thermoplastic film material is sufficiently high to achieve sterility between the film layers, and the lack of oxygen between each of the film layers enables the sterility to be maintained. Thus, the visor system does not need to be pre-sterilized prior to incorporating the visor system into a sterile protective garment.

In other words, utilizing the coextrusion approach contemplated by the visor system of the present invention allows the formation of a multi-layer visor system that is sterile between each of the layers upon formation of the visor film, which is in stark contrast to current film attachment methods that utilize adhesives. Because ethylene oxide gas cannot penetrate films bonded together via adhesives and cannot penetrate polyester and polycarbonate transparent films, unlike the visor system of the present invention, currently available visor systems often require the use of radiation sterilization (e.g., gamma radiation) as an interim step to sterilize the visor system separately before the visor system can be incorporated into a surgical hood, which is then sterilized by, for instance, EO gas, resulting in a very inefficient and time-consuming sterilization process.

On the other hand, the coextruded film layers contemplated by the present invention allow the high temperature of the coextrusion process to kill biological indicator (BI) microbes to yield an underlying sterile surface of each film layer. The resulting multi-layer visor system of the present invention can thus be formed and then bonded or otherwise attached to a surgical hood or a surgical gown with attached hood, and the entire protective surgical garment can then be sterilized in one step via exposure to ethylene oxide gas, rather than having to sterilize the individual components in multiple steps as required for currently available multi-layer visor systems. This is because the intermediate surfaces of the layers of film of the visor system are sterile upon coextrusion of the film due to the high temperatures of coextrusion, and the inner and outer surfaces of the visor system are then sterilized by ethylene oxide gas along with the rest of the protective surgical garment. This results in a surgical hood and/or gown where all of the transparent films (e.g., the base film and one or more removable films) are sterile in the event that one or more of the outermost transparent films are peeled away from the visor system and discarded as they become soiled.

In addition, it is to be understood that the visor system of the present invention contemplates placement of one or more peel-away tabs for removal of each of the removable film layers around the perimeter of the removable transparent films of the visor system so as to be unobtrusive to the surgeon or other healthcare provider. Moreover, the various transparent films are attached to each other with a bond strength sufficient to secure the transparent films to each other when in use, while also allowing for the surgeon or other healthcare provider to easily peel away and remove an outermost soiled transparent film without dislodging the other layers and the underlying helmet to which the surgical hood and visor system is secured.

The specific features of the visor system and methods of manufacturing of the present invention are discussed in more detail and may be better understood with reference to FIGS. 1-8.

Figure 2:
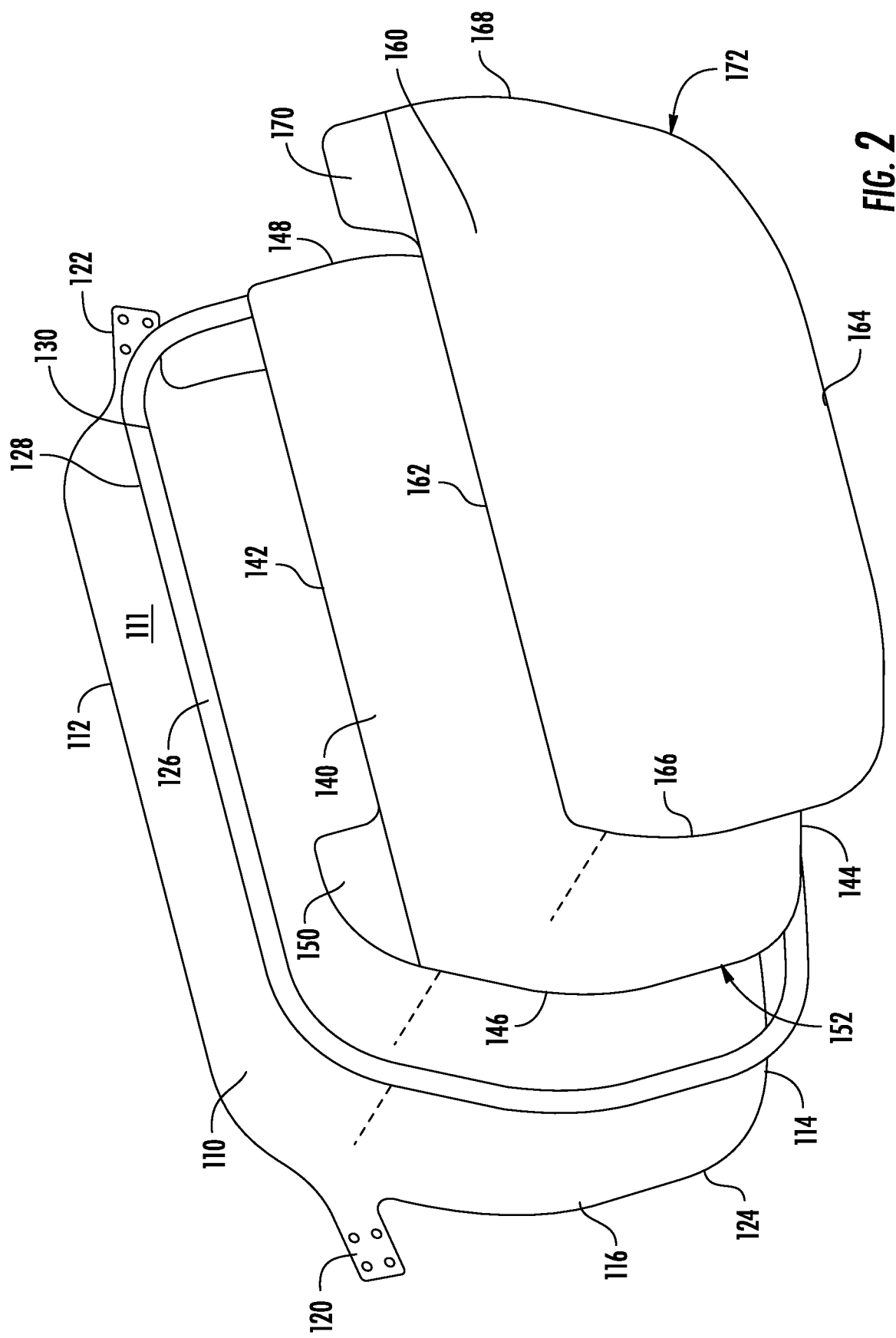
FIG. 2 illustrates an exploded view of the visor system of FIG. 1.

Referring now to FIG. 1, a front view of one visor system 100 contemplated by the present invention is shown. The visor system 100 includes a base film 110 having a perimeter 124 including an upper side 112, a lower side 114, a first lateral side 116, a second lateral side 118, and an outer-facing surface 111 (see FIG. 2) that is the surface facing away from the wearer's face and may be exposed to the environment when incorporated into a surgical hood and an inner-facing surface (not shown) that is the surface closest to a wearer's face when incorporated into a surgical hood. The base film 110 can include tabs 120 and 122 extending from a first lateral side 116 and a second lateral side 118 of the visor system 100. Tabs 120 and 122 can be used to secure the visor system 100 to a surgical hood, such as the surgical hood 10 shown in FIG. 6. The visor system 100 also includes at least one removable film, e.g., a plurality of removable films, configured to be easily peeled away to expose a clean film layer underneath. For instance, the visor system 100 can include at least a first removable film layer 140 having a perimeter 152 that can be contained completely within the perimeter 124 of the base film layer 110, as shown in FIG. 1. For instance, as shown in FIGS. 1-2, the visor system 100 includes a first removable film layer 140, and a second removable film layer 160, where the second removable film layer 160 has a perimeter 172 that can be contained completely within the perimeter 124 of the base film layer 110. The plurality of removable film layers, e.g. removable film layers 140 and 160, can each include tabs (e.g., tabs 150 and 170, respectively) that enable the wearer to peel-away the outermost removable film layer 140 or 160 when it becomes soiled or when the wearer's visibility is otherwise diminished due to the presence of blood, tissue, or other matter coming into contact with the film layer 140 or 160.

Figure 5:
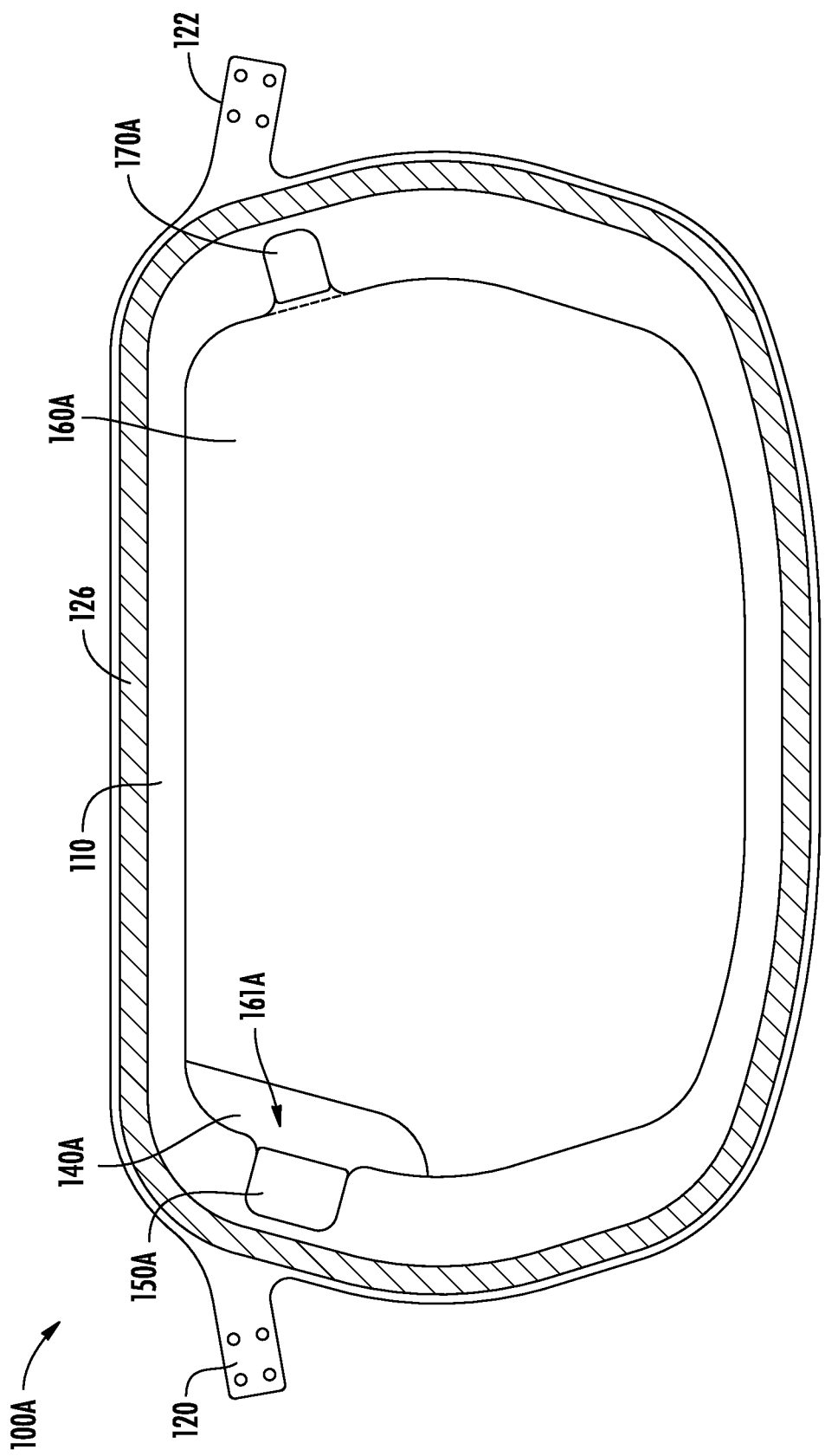
FIG. 5 illustrates a front view of a visor system of the present invention having an alternative arrangement of peel-away layers.

As shown in FIGS. 1-2, in some embodiments, the tabs 150 and 170 can be present on opposite sides of the visor system 100, e.g., the tab 150 of the first removable film layer 140 can be adjacent to the first lateral edge 116 of the base film layer 112 and the tab 170 of the second removable film layer 160 can be adjacent to the second lateral edge 118 of the base film layer 110. Meanwhile, in other embodiments (not shown), both tabs 150 and 170 can both be present on the same side of the visor system 100. The tabs 150 and 170 can be present on an upper side of each of the removable film layers 140 and 160, respectively, or on one or both of the lateral sides of the removable film layers 140 and 160, such that neither of the tabs 150 or 170 occludes a wearer's field of view through the visor system 100. FIG. 5 illustrates another alternative arrangement of a visor system 100A having a first removable film layer 140A having a tab 150A on one lateral side of the first removable film layer 140A, and a second removable film layer 160A having a tab 170A on an opposite lateral side of the second removable film layer 160A. Optionally, as shown in FIG. 5, the second removable film layer 160A can include a cut-away section 161A on the lateral side opposite the tab 170A and aligned with the tab 150A of the first removable film layer 140A in order to expose the tab 150A and first removable film layer 140A to be able to easily distinguish between the removable layers.

As shown in FIG. 1, the base film 110 can have a height H1 in the y-direction ranging from about 5 inches (in) (13 centimeters or cm) to about 15 in (38 cm), such as from about 6.5 in (16.5 cm) to about 13 in (33 cm), for example from about 8 in (20 cm) to about 11 in (28 cm).

Meanwhile, the first removable film layer 140 can have a height H2 in the y-direction, including the tab 150, ranging from about 4 in (10 cm) to about 13 in (33 cm), such as from about 6 in (15 cm) to about 11 in (28 cm), for example from about 7 in (17.5 cm) to about 10 in (25 cm). When measured without including the tab 150, the first removable film layer 140 can have a height H3 in the y-direction extending from the upper edge 142 to the lower edge 144 ranging from about 3 in (7.5 cm) to about 12 in (30.5 cm), such as from about 4 in (10 cm) to about 11 in (28 cm), for example from about 5 in (13 cm) to about 9 in (23 cm).

The second removable film layer 160 can also have a height H3 in the y-direction including the tab 170 ranging from about 3 in (7.5 cm) to about 12 in (30.5 cm), such as from about 4 in (10 cm) to about 11 in (28 cm), for example from about 5 in (13 cm) to about 9 in (23 cm), i.e., the height of the second removable film layer 160 including tab 170 can be approximately equal to the height of the first removable film layer 140 excluding the tab 150. When measured without including the tab 170, the second removable film layer 160 can have a height H4 in the y-direction ranging from about 2 in (5 cm) to about 11 in (28 cm), such as from about 3 in (7.5 cm) to about 10 in (25 cm), for example from about 4 in (10 cm) to about 8 in (20 cm).

In addition, the base film layer 110 can have an overall width W1 in the x-direction including the tabs 120 and 122 ranging from about 13 in (33 cm) to about 23 in (58 cm), such as from 14 in (35.5 cm) to about 22 in (56 cm), for example from about 15 in (38 cm) to about 20 in (51 cm), and a width W2 in the x-direction excluding the tabs 120 and 122 ranging from about 11 in (28 cm) to about 20 in (51 cm), such as from about 12 in (30.5 cm) to about 19 in (48 cm), such as from about 14 in (35.5 cm) to about 17 in (43 cm).

Moreover, the first removable film layer 140 and the second removable film layer 160 can each have a width W3 in the x-direction ranging from about 9 in (23 cm) to about 18 in (46 cm), such as from about 10 in (25 cm) to about 17 in (43 cm), for example from about 12 in (30.5 cm) to about 15 in (38 cm).

Additionally, the tabs 150 and 170 can have a width W4 ranging from about 0.5 in (1.3 cm) to about 3.5 in (9 cm), such as from about 1 in (2.5 cm) to about 3 in (7.6 cm), for example from about 1.5 in (3.8 cm) to about 2.5 in (6.5 cm).

Further, regardless of the dimensions of each of the film layers 110, 140, and 160, or the number of removable films present in the visor system 100, the films can each be transparent and can each be formed from polycarbonate or polyester. In one particular embodiment, the films 110, 140, and 160 can be polyester. For instance, the films can be formed from clear polymer polyethylene terephthalate, commonly referred to as PET. PET is thermoplastic, i.e., it softens and melts at high temperatures.

Figure 3:
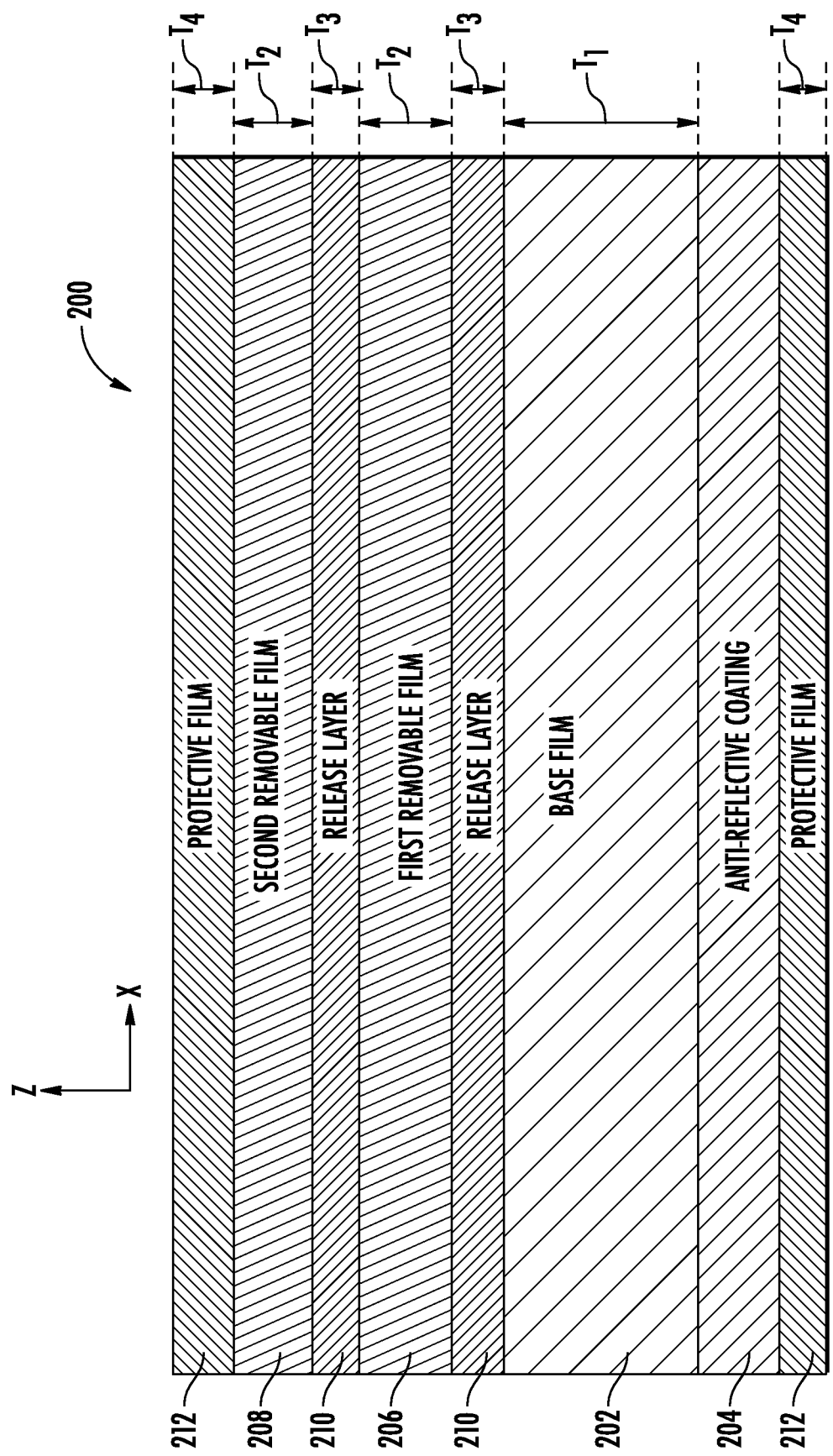
FIG. 3 illustrates a schematic diagram of the layers of the coextruded visor film according to one particular embodiment of the present invention.

The films according to the invention can be manufactured in various ways. A preferred manufacturing method uses coextrusion, for example through flat film coextrusion. Furthermore, both individual and all coatings of the film according to the invention can be formed by extrusion, particularly through flat film coextrusion. Referring now to FIG. 3, in flat film coextrusion of the visor film 200, molten polymer, e.g., polyester, is cast through multiple extruders and die slots, e.g., flat dies, that meet at an exit opening, to adopt its flat film shape. The coextrusion process can deliver polymer, e.g., polyester, at a range of melt temperatures and viscosities/densities that cool differentially. The coextruded films 202, 206 and 208 can be connected by ultra-thin tie layers that provide adhesion to the surface adjacent to it (i.e., between the base film 202 and the first removable film 206, and between the first removable film 206 and the second removable film 208, respectively) while maintaining ease of release between the films 202, 206, 208 in the final multi-layered visor film 200.

The visor film 200 may optionally include one or more protective films 212, as shown in FIG. 3, which may form the outermost layers of the visor film 200. The protective film(s) 212 may be formed of any suitable protective thermoplastic film material, e.g., polyethylene film. The protective film(s) 212, when present, can maintain the sterility of the base film 202 and/or the second removable film 208 and protect the integrity of the base film 202 and/or the second removable film 208, e.g., to protect from scratches. In alternative aspects of the invention, the protective film(s) 212 can be applied on either of the outermost layers of the visor film 200 or visor system 100 after the coextrusion of the base film 202, first removable film 206 and second removable film 208 of the visor film 200. For instance, in an embodiment of the visor system 100 (not shown), a protective film 212 may be applied over the second removable film layer 160 after the adhesive gasket 126 has been applied to the base film layer 110, which will be described in greater detail below.

In some aspects of the invention, the melting temperature of the polyester material from which the films 202, 206, and 208 are coextruded can in in a range from about 535 to about 550 degrees Fahrenheit (about 280 to about 288 degrees Celsius). Thus, when coextruded, the layers of molten polyester forming each of the films 202, 206 and 208 is generally at a temperature equal to or greater than the melting temperature of about 535-550 degrees Fahrenheit. The very high melting temperature of the polyester material that is coextruded to form the films 202, 206, 208 that form each of the layers 110, 140 and 160 of the visor system 100 contributes to the sterility of the visor system 100 by ensuring sterility between each of the layers 110, 140 and 160.

For comparison, hospital steam autoclave systems achieve terminal kill at recommended temperatures of about 274-278 degrees Fahrenheit for sterilizing surgical instruments. Sterility is conceptualized as the probability that a pathogenic organism will be present on a product. The safe sterility assurance level ("SAL") required by the Food and Drug Administration for medical devices, or "terminal kill," is $10^{-6}$, meaning a probability of one out of one million devices may contain a single organism. Put another way, terminal kill is generally associated with a 6-log reduction in bacteria.

Thus, by far exceeding the recommended temperature range for terminal kill by coextruding polyester at a melt temperature of from about 535 to about 550 degrees Fahrenheit, and by coextruding the films such that there is no space, e.g., air or oxygen, in between the films, the present inventors have found that coextrusion of the polyester films can achieve a sterile outer surface of the base film 202, which forms the base film layer 110 of the visor system 100, and a sterile outer surface of the first removable film layer 206, which forms the first removable film layer 140 of the visor system 100, without requiring a separate or distinct step of sterilizing the layers of the visor system 100. In a laboratory test for sterility of the coextruded film 200, 20 sample visors 100 formed from the coextruded film 200 were tested for sterility and microbe growth. All 20 visors were confirmed through testing to have no microbe growth and thus confirmed as sterile. Notably, current standards for sterility state that a sample size of 20, as was tested with the 20 visors, is acceptable to establish sterility of a product. Therefore, the visor 100 of the present invention meets sterility standards For instance, as shown in FIG. 3, a visor film 200 may be coextruded including a base film 202, a first removable film 206 and a second removable film 208, which each form the base film layer 110, first removable film layer 140 and second removable film layer 160, respectively, when the visor system 100 is formed. As shown in FIG. 3, the visor film 200 may additionally include a release layer 210 between the base film 202 and the first removable film 206, and between the first removable film 206 and the second removable film 208. The release layer 210 may be a distinct film, as shown in FIG. 3, or it may be one or more additive composition(s) mixed and coextruded with the base film 202, first removable film 206 or second removable film 208. The release layer 210 is configured to enable each of the removable films 206, 208 to separate easily from the respective adjacent layers of film when the visor system 100 is formed. Each of the release layers 210 are configured to be removed along with an outer removable film layer. For instance, when the second removable film layer 140 of the visor system 100 is peeled away, both the second film 208, which forms the second removable film layer 140 of the visor system 100, and the release layer 210 immediately adjacent to the second film 208 as shown in FIG. 3, are peeled away together.

Further, as shown in FIG. 3, the base film layer 110 formed from the base film 202 of the visor film 200 can have a film thickness T1 in the z-direction ranging from about 150 micrometers (6 mils) to about 350 micrometers (14 mils) (1 mil is 0.001 inches), such as from about 175 micrometers (7 mils) to about 325 micrometers (13 mils), such as from about 200 micrometers (8 mils) to about 300 micrometers (12 mils). In one particular embodiment, the base film layer thickness T1 may be about 250 micrometers (about 10 mils). The removable film layers 140 and 160 formed from the removable films 206 and 208 of the visor film 200 can each have a thickness T2 in the z-direction ranging from about 10 micrometers (0.4 mils) to about 125 micrometers (5 mils), such as from about 25 micrometers (1 mil) to about 100 micrometers (4 mils), such as from about 30 micrometers (1.2 mils) to about 70 micrometers (3 mils). In one particular embodiment, the removable film layers 140 and 160 can each have a thickness T2 of about 50 micrometers (about 2 mils). The release layers 210 of the visor film 200 can account for a thickness T3 in the z-direction of the film 200 in a range from about 5 micrometers (0.2 mils) to about 25 micrometers (1 mil). Additionally, when present, the protective film(s) 212 can have a thickness T4 in the z-direction in a range from about 19 micrometers (0.75 mils) to about 38 micrometers (about 1.5 mils). A total thickness T5 of the multi-layer visor system 100 in the z-direction, as measured, e.g., using calipers, can be in a range from about 250 micrometers (about 10 mils) to about 400 micrometers (about 16 mils).

When viewing through the visor system 100 having base film layer 110 and a plurality of removable film layers, e.g., 140 and 160, the visor system 100 appears to be one single piece of plastic film. The present inventors have found that the transparency, i.e., the percentage of transmission of light, of the visor system 100 is inversely related to the number of layers of film(s) used to form the visor system 100. Thus, a visor system 100 having fewer layers generally may have a higher percentage of light transmission than a visor system having a greater number of layers. In order to provide a sufficient field of view for a surgeon or other user of the visor system 100 of the present invention, the visor system 100 has a target light transmission percentage of about 85% or greater, such as about 88% or greater, for instance about 90% or greater. In addition, a high value of clarity is necessary in order to provide a sufficient field of view for a surgeon or other user of the visor system 100 of the present invention. The visor system 100 has a target clarity percentage of about 95% or greater, such as about 96% or greater, for instance about 97% or greater. The present inventors have found that the desire of the surgeons or other users of the visor system 100 for removable peel-away layers is balanced with the criticality of the transparency and clarity of the visor system 100 for the surgeons and/or other users, e.g., to be able to have a clear field of view to perform a surgery or other medical procedure. The visor system of the present invention may generally include a number of peel-away film layers, such as from one (1) to about four (4) peel-away layers while maintaining at least about 88% light transmission and at least about 96% clarity.

Typical polyester film reflects back incident light by about 8-11% and is sufficient to cause eye strain/fatigue. Thus, an anti-reflective coating 204 may be applied, e.g., aqueously applied, or coextruded on the inner-facing surface of the base film 202 as shown in FIG. 3. The anti-reflective coating 204 is configured to reduce glare of the visor system 100. Glare is caused by a significant ratio of luminance between the task (that which is being looked at) and the glare source, e.g., light source. In some aspects, the anti-reflective coating 204 may be an anti-reflective and anti-fog coating for reducing both glare and fogging of the visor system 100. For example, one particular anti-reflective, anti-fog coating that may be applied to the base film 202 is the AFAR anti-fog anti-reflective offered by 3M™. The AFAR technology has greater than 80% light absorption, thereby significantly reducing glare.

After the formation of the visor film 200, e.g., by coextrusion as described above, the visor system 100 may be formed by cutting each of the individual layers 110, 140 and 160 from the visor film 200. One such method is die-cutting or kiss-cutting of the visor film 200 to form the visor layers

110, 140, 160. For instance, a first die-cut in the shape of the perimeter 112 of the base film layer 110 of the visor system 100 may cut through all of the layers of the visor film 200. Then, a second die-cut in the shape of the perimeter 152 of the first removable film layer 140 may cut through the second removable film 208 and the first removable film 206, along with the release layers 210, to form the first removable film layer 140. Next, a third die-cut in the shape of the perimeter 172 of the second removable film layer 160 may cut through just the second removable film 208 and its adjacent release layer 210 to form the second removable film layer 160. Thus, each of the film layers 110, 140 and 160 of the visor system 100 may be die-cut from the visor film 200, each having distinct shapes and dimensions, as described above and illustrated in FIGS. 1-2. In other aspects of the invention, the visor system 100 may be formed from the visor film 200, e.g., by laser cutting each of the layers 110, 140, and 160 in the desired shape, or any other suitable method that is capable of cutting each of the layers 110, 140, and 160 to shape from the visor film 200.

Figure 4A:
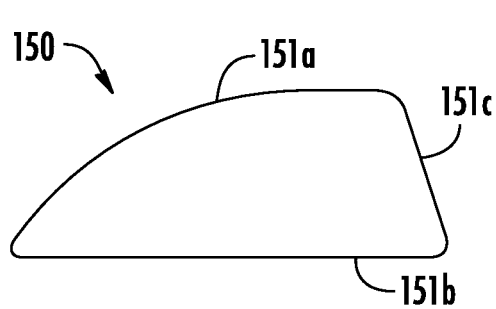
FIGS. 4A-D each illustrates a front view of embodiments of a peel-away tab of the visor system of FIG. 1.
Figure 4B:
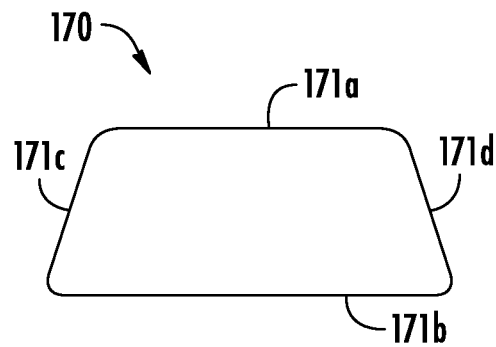

Turning next to FIGS. 4A-E, the tabs 150 and 170 of the first removable film layer 140 and second removable film layer 160, respectively, may be formed having different shapes, colors, textures, and/or other distinctive features in order to enable a wearer to easily distinguish between the tabs 150 and 170. Thus, it can be easier for a wearer to know which tab to pull first to remove the outermost, i.e., second removable film layer 160, using the tab 170. For instance, as is shown in FIGS. 1-2, 4A and 4B, the tab 150, shown in detail in FIG. 4A, has a different shape than the tab 170, shown in detail in FIG. 4B. For instance, the tab 150 may be a three-sided shape having an upper side 151*a*, a lower side 151*b* adjacent to the first removable film layer 140 as shown in FIGS. 1-2, and a lateral side 151*c*. The upper side 151*a* may be sloped between an upper end of the lateral side 151*c* to an opposite end of the lower side 151*b* as shown in FIG. 4A. In contrast, the tab 170 may be a four-sided tab having an upper side 171*a*, a lower side 171*b* adjacent to the second removable film layer 160, a first lateral side 171*c* and a second lateral side 171*d*. The first and second lateral sides 171*c* and 171*d* may each connect between the upper side 171*a* and the lower side 171*b* such that the tab 170 forms a generally quadrilateral shape, e.g., a rectangular shape or a trapezoidal shape. Thus, the different shapes of the tabs 150 and 170 can help a user distinguish between the two tabs in order to determine which tab should be pulled first.

In addition, the second tab 170 may be formed having a first color, and the first tab 150 may be formed having a second color, where the second color is different from the first color. Ideally, the second color is visually contrasting to the first color in order to easily distinguish between the two colors. The colors of each of the tabs 150 and 170 may be formed from colored tapes of two distinct colors, e.g., coextruded with the visor film 200 or attached to the removable film layers 140 and 160 after cutting the visor system 100 from the visor film 200.

Figure 4C:
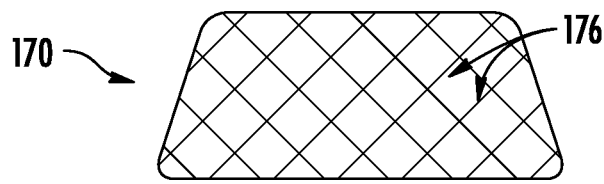

The tabs 150 and/or 170 can additionally be formed having different textures so that a wearer can distinguish between the tabs based on tactile feel. For instance, the tab 170 can include textured elements 176 as shown in FIG. 4C, while the tab 150 may be smooth without any textured elements. The textured elements 176 can be formed on the tab by any suitable means, e.g., coextrusion during formation of the visor film 200, printing, imprinting, or otherwise additive manufacturing, molding, or any other suitable means of achieving a textured surface. Generally, the outer-facing surface of the tab is provided with textured elements 176 so that a wearer may feel the textured elements 176, although in some aspects, both surfaced of the tab may be provided with textured elements 176. The textured elements 176 may be disposed in a pattern, e.g., lines such as straight or curved lines, dashes, dots and/or a dash-dot pattern, circles, swirls, checkered pattern, diagonal pattern, or any other pattern, or the textured elements 176 may be applied randomly with no uniform pattern formed.

Figure 4D:
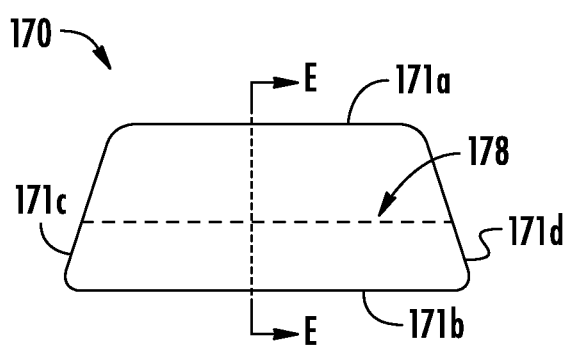
Figure 4E:
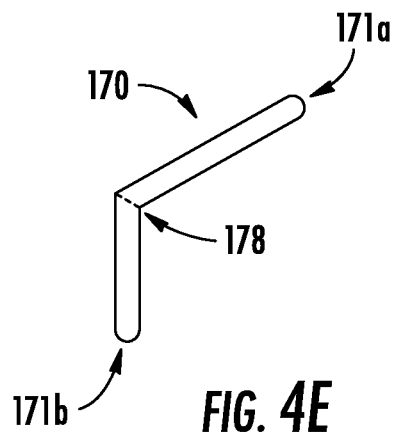
FIG. 4E illustrates a cross-sectional view of the peel-away tab of FIG. 4D.

As illustrated in FIGS. 4D-4E, one or more of the tabs, e.g., tab 170, may additionally include a crease 178 along which the tab 170 may be folded or creased in order to form a three-dimensional shape, as shown in FIG. 4E, which is a cross-sectional view of the tab 170 of FIG. 4D taken along the line E-E. The tab may include one or more creases 178. For instance, a plurality of creases 178 may be used to form a crinkled or uneven texture. The crease 178 as shown in FIGS. 4D-E can enable a wearer to more easily locate and grasp the tab 170, e.g., by folding the upper side 171*a* of the tab 170 in a direction away from the visor system 100. The crease 178 can form an angle in a range from about 20 degrees to about 100 degrees, such as from about 30 degrees to about 90 degrees, for instance about 45 degrees to about 60 degrees.

Turning back to FIGS. 1-2, an adhesive gasket 126 may be applied to the base film layer 110. The adhesive gasket 126 is configured to adhere the visor system 100 to a surgical hood, e.g., as shown in FIG. 5. The adhesive gasket 126 is defined by an inner perimeter 130 and an outer perimeter 128, whereby the inner perimeter 130 surrounds the perimeter 152 of the first removable film layer 140 such that the removable film layers 140, 160 remain fully exposed when the visor system 100 is attached to the surgical hood 10. The adhesive gasket 126 can be formed from any suitable adhesive material. For instance, a hot-melt adhesive, e.g., a low temperature polyolefin hot melt adhesive or glue, may be used. Alternative adhesives may include pressure-sensitive adhesive or heat-activated adhesive. After applying the adhesive gasket 126 to the base film layer 110 but prior to attaching the visor system 100 to the surgical hood 10, a protective film 212 may be placed over the visor system 100 in contact with the adhesive gasket 126 in order to protect the outer layer, e.g., second removable film layer 160, of the visor system and the adhesive gasket 126 until the surgical hood 10 is ready for assembly.

Figure 6:
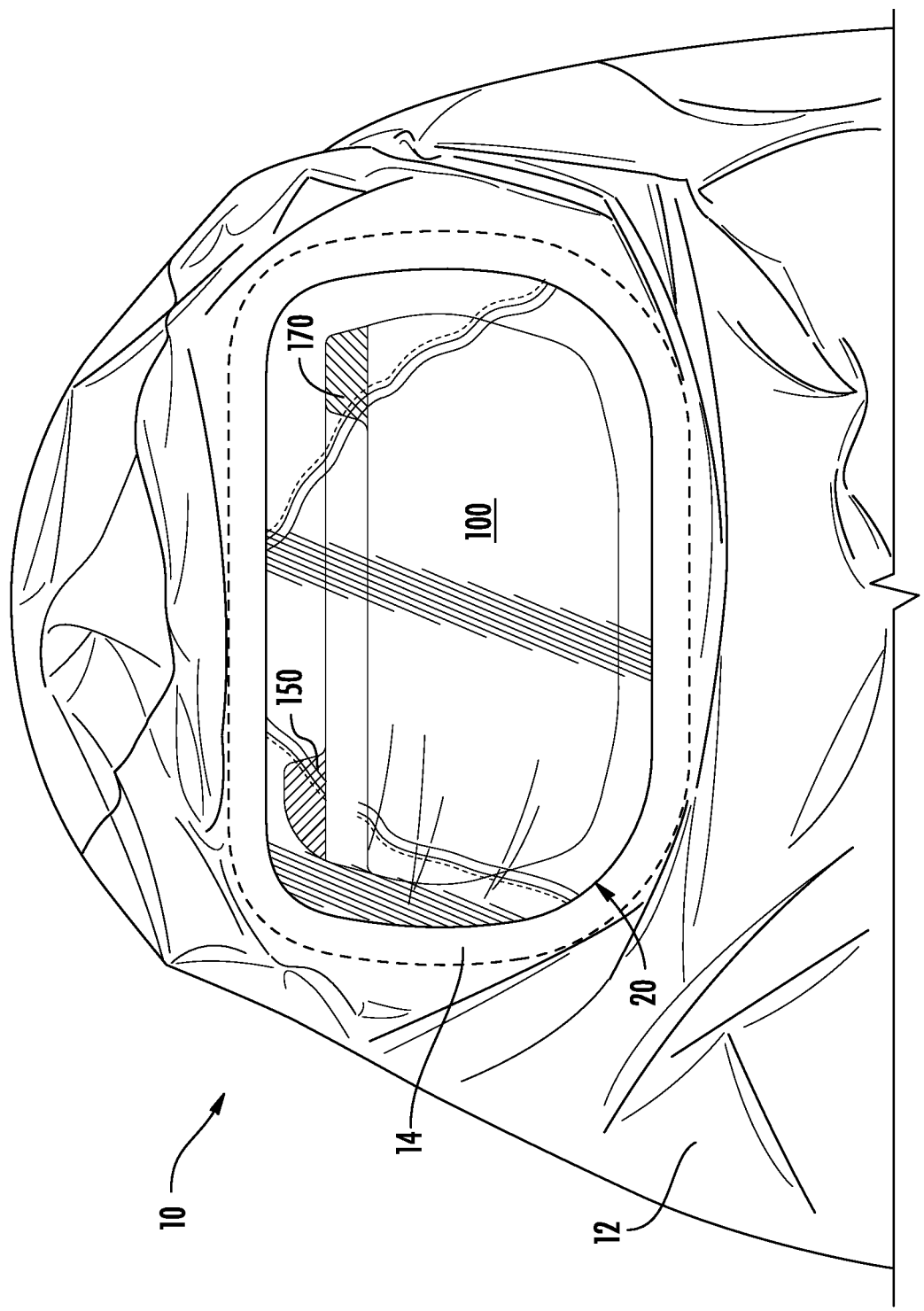
FIG. 6 illustrates a surgical hood incorporating the visor system of FIG. 1.

During assembly, or conversion, of the visor system 100 into a surgical hood 10 as shown in FIG. 6, the protective film 212 adjacent to the second removable film layer 160 can be removed to expose the adhesive gasket 126. Then, the visor system 100 can be inserted into an interior portion of a surgical hood 10 or other medical helmet or garment. For instance, the surgical hood 10 can be made of a nonwoven barrier fabric, e.g., a polypropylene nonwoven fabric 12. The surgical hood 10 can include a cut-out area 20 configured to receive the visor system 100 which is surrounded by an attachment region 14. The adhesive gasket 126 is then adhered to the attachment region 14 on the inner portion of the surgical hood 10, as shown in FIG. 6. After assembling the surgical hood 10, a protective film 212 on the inner side of the base film layer 110, if present, is removed. Then, the surgical hood 10 is ready for final packaging and sterilization. The entire protective surgical garment, e.g., surgical hood 10 including the visor system 100, can then be sterilized in one step via exposure to ethylene oxide gas. The EO gas penetrates and sterilizes the nonwoven fabric of the surgical hood 10 as well as the exposed surfaces of the visor system 100, while the inner layers of the visor system 100 remain sterilized due to the high temperatures of coextrusion of the visor film 200 from which the visor system 100 is formed. This results in a surgical hood and/or gown where all of the transparent films (e.g., the base film and one or more removable films) are sterile in the event that one or more of the outermost transparent films are peeled away from the visor system and discarded as they become soiled. Due to the sterility of the inner layers of the visor system 100 resulting from the high temperatures of coextrusion of the visor film 200, as described above, there is no need for pre-sterilization of the visor system 100 prior to assembling the surgical hood 10.

Figure 7:
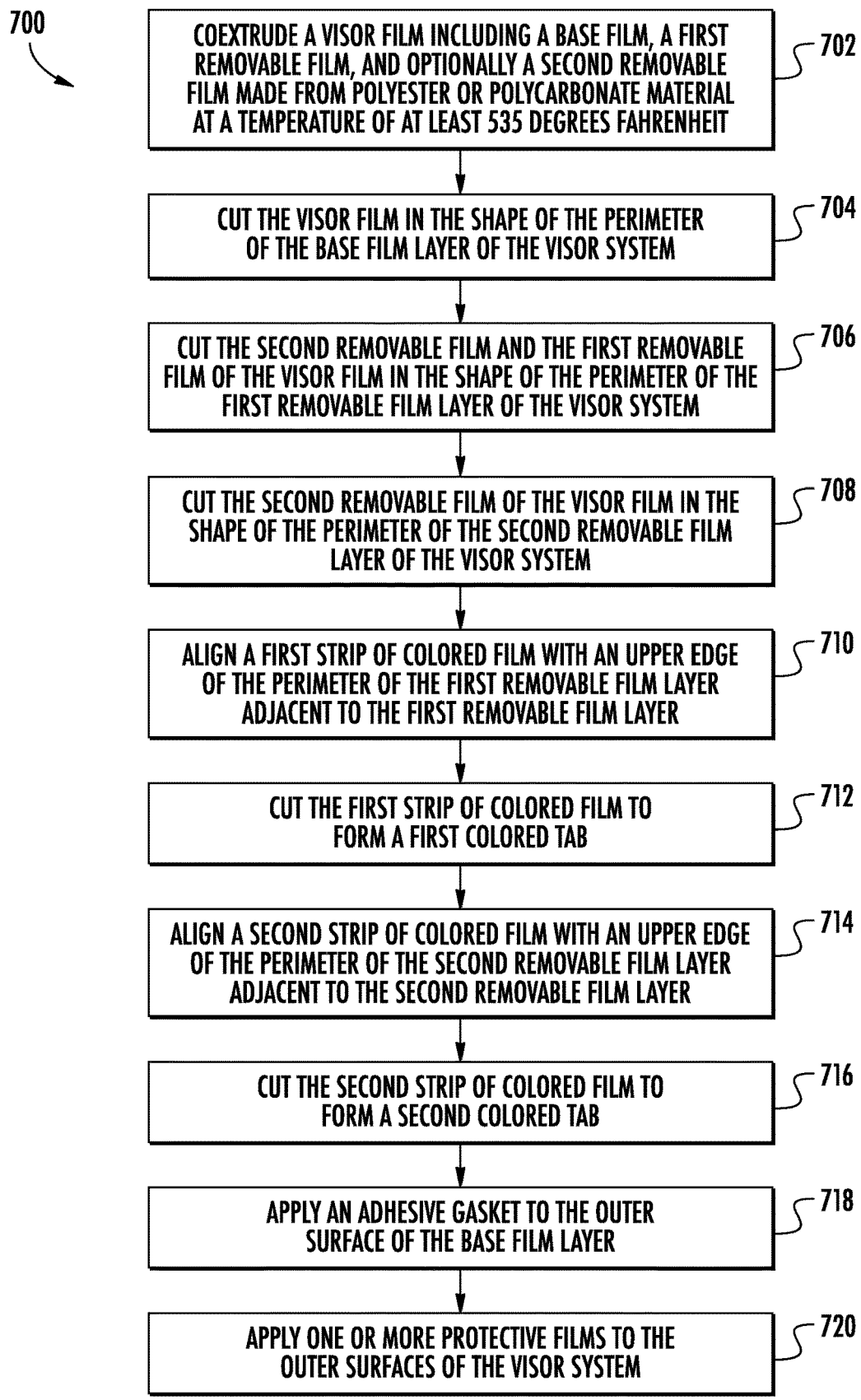
FIG. 7 illustrates a flowchart of method steps of a method for manufacturing a visor system according to the present invention.

As shown in FIG. 7, the present invention is further directed to a method of manufacturing a multi-layer visor system and a protective surgical garment incorporating the multi-layer visor system. In step 702, a visor composite film including a base film and a first removable film is coextruded. Optionally, a second removable film is also coextruded in the formation of the visor composite film. The base film, first removable film, and second removable film are formed from thermoplastic polyester or polycarbonate material having a melting temperature in a range from about 535 degrees Fahrenheit to about 550 degrees Fahrenheit (about 280 to about 288 degrees Celsius). The coextrusion step 702 is carried out at a temperature greater than the melting temperature, i.e., at least about 535 degrees Fahrenheit. Then, beginning in step 704, the visor system 100 is cut out from the visor composite film. Specifically, in step 704, each layer of the visor composite film is cut in the shape of the perimeter of the base film layer. Then, in step 706, the first removable film and the second removable film, if present, are cut in the shape of the perimeter of the first removable film layer. Optionally, the perimeter 152 of the first removable film layer 140 includes the shape of the first tab 150. Next, in step 708, the second removable film is cut in the shape of the perimeter of the second removable film layer, resulting in a visor system 100 having two removable film layers such that the perimeters 152 and 172 of both the first removable film layer 140 and the second removable film layer 160, respectively, are contained within the perimeter 124 of the base film layer 110. Optionally, the perimeter 172 of the second removable film layer 160 includes the shape of the first tab 170. Further, the shape of the first tab 150 and the shape of the second tab 170 may be different or distinct from each other to enable a user to easily distinguish between the first tab 150 and the second tab 170. Moreover, due to the high temperature at which the coextrusion step 702 is carried out, an outer surface of the base film layer 110 adjacent to the first removable film layer 140 and an outer surface of the first removable film layer 140 adjacent to the second removable film layer 160 are sterile as manufactured, without any need for an additional or separate step of sterilizing the layers of the visor system 100. In some aspects of the method, the cutting performed in steps 704, 706 and 708 can be done by die-cutting, e.g., kiss-cutting, or by laser cutting, or any other suitable means for cutting through some but not all layers of a film.

Then, in step 710, a first strip of colored film may be aligned with an upper edge 142 of the perimeter 152 of the first removable film layer adjacent to the first removable film layer 140. In step 712, the first strip of colored film is cut to form a first colored tab 150 along the upper edge 142 of the perimeter 152 of the first removable film layer 140. The first colored tab is configured to facilitate removal of the first removable film from the base film by a user. Next, in step 714, a second strip of colored film may be aligned with an upper edge 162 of the perimeter 172 of the second removable film layer 160 adjacent to the first removable film layer.

In step 716, the second strip of colored film is cut to form a second colored tab 170 along the upper edge 162 of the perimeter 172 of the second removable film layer 160. The second colored tab 170 is configured to facilitate removal of the second removable film 160 from the visor system 100 by a user.

In step 718, an adhesive gasket 126 is applied to an outer surface of the base film layer 110 having an adhesive gasket inner perimeter 130, which surrounds the perimeter 152 of the first removable film layer 140, and an adhesive gasket outer perimeter 128, which is contained within the perimeter 124 of the base film layer 110. In step 720, one or more protective films 212 are applied to the outer surfaces of the visor system 100 to protect the layers of the visor system 100 and the adhesive gasket 126.

Figure 8:
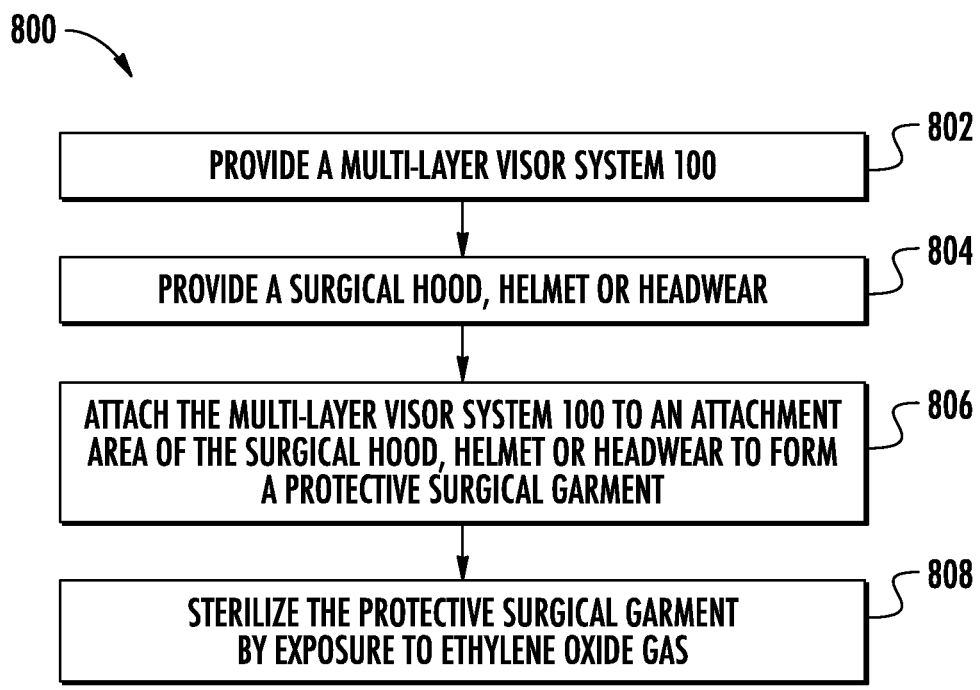
FIG. 8 illustrates a flowchart of method steps of a method for manufacturing a sterile protective garment including the visor system of the present invention.

As shown in FIG. 8, the invention is further directed to a method of manufacturing a sterile protective surgical hood that includes the visor system 100. In step 802, the visor system 100 as described above and shown in FIGS. 1-2 is provided. For instance, the visor system 100 may be manufactured according to the method 700 shown in FIG. 7. An outer-facing surface of the base film layer 110 of the visor system 100 is sterile due to the high temperature at which the base film layer 110 was extruded along with the first removable film layer 140 and the second removable film layer 160. Thus, no step of pre-sterilization of the visor system 100 is needed. Next, a surgical hood comprising a nonwoven fabric material, or a helmet or other protective headwear, is provided in step 804. If not already present, a visor aperture is cut out of the surgical hood, helmet, or headwear. In step 806, the multi-layer visor system 100 is attached to an attachment area 14 of the surgical hood, helmet or headwear to form a protective surgical garment. The adhesive gasket 126 of the multi-layer visor system 100 is used to attach to the attachment area 14. Then, in step 808, the entire protective surgical garment is sterilized in a single package, e.g., by exposure to ethylene oxide gas. In other words, by using the visor system 100 made from a coextruded visor film 200 as described above, which results in sterile inner surfaces of each visor layer, the entire protective surgical garment may be sterilized in one single sterilization step without any need for pre-sterilization of the visor system 100.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. A multi-layer visor system for a personal protection system, the visor system comprising:
   a base film layer;
   one or more removable film layers, wherein a first removable film layer of the one or more removable film layers is releasably coupled to an outer-facing surface of the base film layer;
   a release layer disposed between the base film layer and the first removable film layer, wherein the release layer is configured to enable separation of the first removable film layer from the outer-facing surface of the base film layer, wherein the release layer does not comprise an adhesive;

a first protective film releasably coupled to an inner-facing surface of the base film layer and a second protective film releasably formed over an outermost removable film layer of the one or more removable film layers;

wherein the base film layer and the first removable film layer are both formed from a first material, wherein the first material is a thermoplastic material;

wherein the first protective film and second protective film are formed from a second material, wherein the second material is different from the first material; and wherein the base film layer, the release layer and the first removable film layer are coextruded.

2. The multi-layer visor system of claim 1, wherein the base film layer defines a perimeter and the first removable film layer defines a perimeter, wherein the perimeter of the first removable film layer is contained completely within the perimeter of the base film layer.

3. The multi-layer visor system of claim 1, wherein the outer-facing surface of the base film layer is sterile.

4. The multi-layer visor system of claim 1, wherein the base film layer comprises a polyester or a polycarbonate.

5. The multi-layer visor system of claim 1, wherein the first removable film layer comprises a polyester or a polycarbonate.

6. The multi-layer visor system of claim 1, further comprising an anti-reflective coating applied to an inner-facing surface of the base film layer.

7. The multi-layer visor system of claim 1, wherein the first removable film layer includes a tab, wherein the tab facilitates removal of the first removable film layer from the base film layer.

8. The multi-layer visor system of claim 1, wherein the first removable film layer comprises a transparent viewing portion and a colored tab portion.

9. The multi-layer visor system of claim 1, wherein the one or more removable film layers comprises a second removable film layer releasably coupled to an outer-facing surface of the first removable film layer;

wherein the first removable film layer and the second removable film layer are coextruded.

10. The multi-layer visor system of claim 9, wherein the base film layer defines a perimeter and the second removable film layer defines a perimeter, wherein the perimeter of the second removable film layer is contained completely within the perimeter of the base film layer.

11. The multi-layer visor system of claim 9, wherein an outer-facing surface of the first removable film layer is sterile.

12. The multi-layer visor system of claim 9, wherein the second removable film layer comprises a polyester or a polycarbonate.

13. The multi-layer visor system of claim 9, wherein the second removable film layer includes a tab, wherein the tab facilitates removal of the second removable film layer from the first removable film layer.

14. The multi-layer visor system of claim 13, wherein the first removable film layer includes a tab;

further wherein the tab of the first removable film layer is visually distinct from the tab of the second removable film layer.

15. A surgical hood comprising the multi-layer visor system of claim 1, wherein the surgical hood and the multi-layer visor system are sterile, wherein the surgical hood comprises a nonwoven fabric material.

16. A surgical gown comprising an integrated surgical hood and the multi-layer visor system of claim 1, wherein the surgical gown, the integrated surgical hood, and the multi-layer visor system are sterile, wherein the integrated surgical hood comprises a nonwoven fabric material.

17. A personal protection system including a surgical gown and a separate surgical hood comprising the multi-layer visor system of claim 1, wherein the personal protection system is ethylene gas sterilized in a single package, wherein the surgical hood comprises a nonwoven fabric material.

* * * * *